United States Patent
Bouvier et al.

(10) Patent No.: US 6,410,578 B1
(45) Date of Patent: Jun. 25, 2002

(54) BENZAZOLE COMPOUNDS AND THEIR USE

(75) Inventors: Jacques Bouvier, Neuchatel; Catherine Christinaz, Gletterens, both of (CH); Olivier Froelich, Kembs (FR)

(73) Assignee: Novartis Animal Health US, Inc., Greensboro, NC (US)

( * ) Notice: Subject to any disclaimer, the term of this patent is extended or adjusted under 35 U.S.C. 154(b) by 0 days.

(21) Appl. No.: 09/699,274

(22) Filed: Oct. 27, 2000

(30) Foreign Application Priority Data

Jun. 18, 1998 (CH) ............................................. 1320/98

(51) Int. Cl.[7] ..................... A61K 31/428; A61K 31/423; A61P 33/14; A01N 43/78; A01N 43/76
(52) U.S. Cl. ....................... 514/367; 514/375; 514/366; 424/405
(58) Field of Search ................................ 514/367, 830, 514/831, 875, 375, 366; 424/405

(56) References Cited

U.S. PATENT DOCUMENTS

| | | | |
|---|---|---|---|
| 3,624,204 A | 11/1971 | Prospekt et al. | 424/244 |
| 3,759,935 A | 9/1973 | De Cat et al. | 260/298 |
| 3,876,791 A | * 4/1975 | Hubbard et al. | 424/270 |
| 4,003,750 A | 1/1977 | Heseltine et al. | 96/129 |
| 4,062,682 A | 12/1977 | Laridon et al. | 96/29 L |
| 4,356,180 A | 10/1982 | McGovern et al. | 424/250 |
| 4,428,957 A | 1/1984 | Boray et al. | 424/270 |
| 4,455,308 A | 6/1984 | Smolanoff | 424/248.57 |
| 4,727,154 A | 2/1988 | Papenfuhs | 548/150 |
| 5,218,002 A | 6/1993 | Stroech et al. | 514/919 |
| 5,601,963 A | 2/1997 | Filosa et al. | 430/217 |

FOREIGN PATENT DOCUMENTS

| | | |
|---|---|---|
| CH | 585 214 | 2/1977 |
| EP | 0 022 653 | 1/1981 |
| GB | 1 425 429 | 6/1973 |
| WO | WO 98/11095 | 3/1998 |

OTHER PUBLICATIONS

Abstracts of JP 05 294828, Nov. 9, 1993, Patent Abstracts of Japan, vol. 18, No. 93, (C–1166), (1994).
Abstracts of JP 09 175926, Nov. 28, 1997, Patent Abstracts of Japan, vol. 97, No. 11, (1997).
Eckstein et al., Chemical Abstracts, No. 5246C, vol. 53, No. 6, (1959).
Bossio et al., Heterocycles, vol. 43, No. 2, "Studies on Isocyanides. 2–Isocyanothioanisole, a Synthetic Equivqlent to the Benzothiazol–2–YL Anion", pp. 471–476, (1996), XP–002119289.
Chaudhuri et al., Indian Journal of Chemistry, vol. 11, "Reactions of Azobenzene–2–sulphenyl Bromide & 2'–Methy;–4∴–nitro–azobenzene–2–sulphenyl Bromide with Alkyl Methyl Ketones & Phenols", pp. 315–317, (Apr. 1973), XP–0021149290.
Chikashita et al., The Chemical Society of Japan, 61, "General Reactivity of 2–Lithiobenzothiazole to various Electrophiles and the Uses as a Formyl Anion Equivalent in the Synthesisi of a–Hydroxy Carbonyl Compounds", pp. 3637–3648, (Oct. 1988), XP–002119288.
Gasco et al., Tetrahedron, vol. 24, "Electronic Absorption Spectra of Condensed Thiazoles and Oxazoles", pp. 5569–5574, (Mar. 25, 1968), XP–002119291.
Taraporewala, Irach B., Tetrahedron Letters, vol. 32, No. 1, "Thiazolo[5,4–b], Acridines and Thiazolo[4,5–b], Acridines: Probable Pharmacophores of Antiviral and Anti––tunor Marine Alkaloids", pp. 39–42, (1991), XP–002119286.
Gallay et al., Derwent Abstracts, 1977–27265Y [16], "Prepn. of anthelmintic (6)–isothiocyano–benzo–thiazoles– from (6)–amino–benzothiazoles", (Feb. 28, 1977), (CH 585214).
Kochhar et al., Ind. J. Med. Res., 62, 1, A Critical Analysis of 'Deet' as a Repellent Against Arthropods of Public Health Importance and Water Leeches, pp. 125–133, (1974).
K.H. Buchel in Chemie der Pflanzenschutz– und Schadlingsbekampfungsmittel; R. Wegler, vol. 1, Springer Verlag Berlin, Heidelberg, New York, 1970, pp. 487 ff.

\* cited by examiner

Primary Examiner—Edward J. Webman
Assistant Examiner—Helen Nguyen
(74) Attorney, Agent, or Firm—Michael U. Lee

(57) ABSTRACT

The present invention discloses a method for repelling insects, mites and ticks from warm-blooded animals with a benzazole compound.

5 Claims, No Drawings

BENZAZOLE COMPOUNDS AND THEIR USE

The invention relates to benzazole compounds, a process for their preparation and their use as insect-, mite- and tick-repellent compositions.

Repellents and deterrents against insects, mites and ticks have the task of deterring harmful or troublesome arthropods from contacting, stinging, sucking or biting areas that are attractive to them, such as the skin of animals and humans, by means of prior treatment of these areas with such compositions.

In the context of the present invention, arthropods are understood to be in particular insects, mites and ticks. These include insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, the vermin which may be mentioned in particular are those which trouble humans or animals and carry pathogens, for example flies such as *Musca domestics, Musca vetustissima, Musca autumnalis, Fannia canicularis, Sarcophaga carnaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobia irritans* and *midges* (Nematocera), such as Culicidae, Simuliidae, Psychodidae, but also blood-sucking vermin, for example fleas, such as *Ctenocephalides felis* and *Ctenocephalides canis* (cat and dog fleas), *Xenopsylla cheopis, Pulex irritans, Dermatophilus penetrans*, lice, such as *Damalina ovis, Pediculus humanis*, biting flies and horseflies (Tabanidae), Haematopota spp. such as *Haematopota pluvialis*, Tabanidea spp. such as *Tabanus nigrovittatus*, Chrysopsinae spp. such as *Chrysops caecutiens*, tsetse flies, such as species of Glossinia, biting insects, particularly cockroaches, such as *Blattella germanica, Blatta orientalis, Periplaneta americana*, mites, such as *Dermanyssus gallinae, Sarcoptes scabiei Psoroptes ovis* and Psorergates spp. and last but not least ticks. The latter belong to the order Acarina. Known representatives of ticks are, for example, Boophilus, Amblyomma, Anocentor, Dermacentor, Haemaphysalis, Hyalomma, Ixodes, Rhipicentor, Margaropus, Rhipicephalus, Argas, Otobius and Ornithodoros and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

Ticks are responsible world-wide for the transmission and spread of many human and animal diseases. Because of their economic influence, the most important ticks are Boophilus, Rhipicephalus, Ixodes, Hyalomma, Amblyomma and Dermacentor. They are carriers of bacterial, viral, rickettsial and protozoal diseases and cause tick-paralysis and tick-toxicosis. Even a single tick can cause paralysis whereby its saliva penetrates into the host animal during ingestion. Diseases caused by ticks are usually transmitted by ticks, which infest several host animals. Such diseases, for example babesiosis, anaplasmosis, theileriasis and heart water disease, are responsible for the death or impairment of a large number of domestic and farm animals in the entire world. In many countries of temperate climate, Ixodide ticks transmit the agent of the chronically harmful Lyme's disease from wild animals to humans. Apart from the transmission of disease, the ticks are responsible for great economic losses in livestock production. Losses are not confined to the death of the host animals, but also include damage to the pelts, loss of growth, a reduction in milk production and reduced value of the meat. Although the harmful effects of a tick infestation on animals have been known for years, and enormous progress has been made using tick-control programmes, until now no completely satisfactory methods of controlling or eliminating these parasites have been found, and in addition, ticks have often developed resistance to chemical active ingredients.

The infestation of fleas on domestic animals and pets likewise represents for the owner a problem which has not yet been satisfactorily resolved. Owing to their complex life cycle, none of the known methods for the control of fleas is completely satisfactory, especially as most known methods are basically directed towards the control of adult fleas in the pelt, and leave completely untouched the different juvenile stages of the fleas, which exist not only in the pelt of the animal, but also on the floor, in carpets, in the bedding of the animal, on chairs, in the garden and all other places with which the infested animal comes into contact. Flea treatment is usually expensive and has to be continued over long periods of time. Success usually depends on treating not only the infested animal, e.g. the dog or cat, but at the same time all the locations which the infested animal frequents.

Such a complicated procedure is unnecessary with the present benzazole derivatives. For a particular advantage of the benzazole derivatives under discussion is that they are extremely effective and at the same time of very low toxicity both for the target parasites and for the warm-blooded animals. This is because their activity is based not on the death of the target parasite, but on the parrying defence thereof (as a repellent or as a deterrent), before it sting, bites or in any other way harms the host organism. The presence of the benzazole derivatives being discussed here appears to disturb the parasites in such a way that they suddenly leave the treated environment without biting or stinging, or even do not infest a treated host animal at all. An additional advantage lies in the long-term action, e.g. compared with DEET (N,N-diethyl-m-toluamide), which although very effective, volatilizes rather rapidly and is therefore often difficult to apply. Usage of the present active ingredients is also pleasant because they are almost odourless.

Numerous active ingredients have already been proposed as repellents/deterrents (e.g. K. H. Büchel in Chemie der Pflanzenschutz—und Schädlingsbekämpfungsmittel; R. Wegler, Vol. 1, Springer Verlag Berlin, Heidelberg, New York, 1970, pp. 487 ff).

3-Methylbenzoic acid diethylamine (DEET), dimethyl phthalate and 2-ethylhexane-1,3-diol are particularly well-known and have been in use for a long time. Of these, DEET has become particularly important in practice (e.g. R. K. Kocher, R. S. Dixit, C. I. Somaya, Ind. J. Med. Res., 62, 1 (1974)).

Benzazoles are known to be used in various fields:

In Tetrah. Lett., 32(1) 1991, on pages 39–41, substituted benzothiazoles are disclosed as intermediates in the preparation of pharmacophores of anti-viral and anti-tumor alkaloids.

Substituted benzothiazoles are also used as intermediates in the preparation of dyes for light-sensitive silver halide emulsions (e. g. U.S. Pat. No. 5,601,963; DE 25 48 184 A and FR A 2 228 090).

6-Isothiocyano-5-methoxy-2-t-butylbenzothiazole is used to control ruminant liver fluke (U.S. Pat. No. 4,428,957), further isothiocyano-benzothiazoles find their use as bactericides, fungicides and anthelminthics (CH 565 164 A and CH 585 214A).

Further benzazoles are mentioned in e. g. Chem. Ber. 101, 1968, pages 4048–56; Bull. Chem. Soc. Japan, 61(10) 1988, pages 3637–48; Heterocycles, 43(2) 1996, pages 471–4; Indian J. Chem., Apr. 11, 1973, pages 315–7; DE 35 28 032 A; Tetrah. 24, 1968, pages 5569–74; DE 20 53 715 A; DE 24 29 562 A; Chem. Abstr., 53(6) 1959, abstract no. 5246c, col 5246 and WO 98 11095 A.

Certain benzimidazoles are disclosed as additives in pest-repellent combinations (Patent Abstracts of Japan 18(93) (C-1166) 1994 & JP 05 294828 A and 97(11) 1997 & JP 09 175926 A).

In addition, urea derivatives and carboxamides having insect-repelling activity are known (e.g. EP-A-22 653; DE-A-27 56 360; U.S. Pat. Nos. 3,624,204; 4,356,180; EP-B1-0 467 045). A considerable disadvantage of the known repellents/deterrents is partly their relatively short duration of activity (usually only a few hours).

Now, new benzazole derivatives of formula I

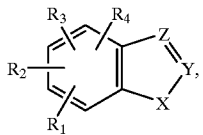

have been found, wherein
  $R_1$ and $R_2$ are the same or different and signify hydrogen, hydroxyl, amino, halogen, $C_1$–$C_6$-alkyl, halogen-$C_1$–$C_6$-alkyl, $C_2$–$C_6$-alkenyl, halogen-$C_2$–$C_6$-alkenyl, $C_3$–$C_6$-cycloalkyl, halogen -$C_3$–$C_6$-cycloalkyl $C_1$–$C_6$-alkoxy, halogen-$C_1$–$C_6$-alkoxy, unsubstituted phenyl or phenyl which is optionally substituted by halogen or $C_1$–$C_6$-alkyl; nitro, cyano, isothiocyanato, carboxy, $C_1$–$C_6$-alkoxycarbonyl, halogen-$C_1$–$C_6$-alkoxycarbonyl, $C_1$–$C_6$-alkylcarbamido, which is optionally substituted by phenyl or by unsubstituted or halogen-substituted phenoxy; PhNH(CO)NH, $C_1$–$C_6$-alkylsulphonyl, halogen-$C_1$–$C_6$-alkylsulphonyl, unsubstituted or optionally halogen-substituted benzoyl; unsubstituted or optionally halogen-substituted phenylthionyl or phenylsulphonyl;
  $R_3$ and $R_4$, independently of one another, are hydrogen, $R_1$, $R_2$ or together are a CH=CH—CH=CH— bridge;
  X is $NR_5$, O or S;
  Y is N, $CR_6$ or C=O;
  $R_6$ is hydrogen, hydroxyl, $C_1$–$C_6$-alkyl, $C_1$–$C_6$-alkylcarbonyl, $C_1$–$C_6$-alkoxy, cyano, 2-di($C_1$–$C_6$alkyd)aminoethenyl, ($C_1$–$C_6$-alkyl)NHC(=S)NHCH$_2$, phenyl, thiazolyl, phenylamino, whereby the phenyl group is unsubstituted or optionally substituted by $C_1$–$C_6$-alkoxy; $C_1$–$C_6$-alkyl-carbamido, $C_1$–$C_6$-alkoxycarbamido, guanidyl, amino, hydroxyl-$C_2$–$C_6$-alkylamino or phenylsulphonylamino, whereby the phenyl group is unsubstituted or optionally substituted by $C_1$–$C_6$-alkyl;
  Z is N or $CR_7$; and
  $R_7$ is hydrogen or $C_1$–$C_6$-alkyl,
which are eminently suitable for long-term repellent/deterrent action against ectoparasites on warm-blooded animals. The repellent/deterrent action is considerably better than that of the repellents/deterrents known from the prior art. The expression ectoparasite as used here has the normal meaning according to the prior art and includes fleas, ticks, lice, mosquitos, horse flies, tsetse flies and other biting flies, especially ticks.

The general terms used hereinbefore and hereinafter, if not defined to the contrary, have the meanings given below.

Halogen—as a group per se and as structural element of other groups and compounds such as halogen-alkyl, halogen-cycloalkyl and halogen-alkenyl—is fluorine, chlorine, bromine or iodine, especially fluorine, chlorine or bromine, in particular fluorine or chlorine.

Halogen-substituted carbon-containing groups, such as halogen-alkyl, halogen-cycloalkyl, halogen-alkenyl, halogen-alkoxy or halogen-alkoxycarbonyl, may be partially halogenated or perhalogenated, whereby in the case of multiple halogenation, the halogen substituents may be identical or different. Examples of halogen-alkyl—as a group per se and as structural element of other groups and compounds such as halogen-cycloalkyl, halogen-alkenyl, halogen-alkoxy or halogen-alkoxycarbonyl,—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; and butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers substituted one to eleven times by fluorine, chlorine and/or bromine, such as $CF(CF_3)(CHF)_2CF_3$ or $CH_2(CF_2)_3CF_3$; and hexyl or one of its isomers substituted one to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

If not defined to the contrary, carbon-containing groups and compounds contain 1 to 6, preferably 1 to 4, especially 1 or 2, carbon atoms.

$C_3$–$C_6$-cycloalkyl is cyclopropyl, cyclobutyl, cyclopentyl or cyclohexyl.

Alkyl—as a group per se and as structural element of other groups and compounds such as alkoxy, halogen-alkyl or halogen-alkoxy—is, in each case with due consideration of the specific number of carbon atoms in the group or compound in question, either straight-chained or branched, and is methyl, ethyl, propyl, isopropyl, butyl, isobutyl, sec.-butyl or tert.-butyl or pentyl, hexyl, or one of the respective isomers thereof. Preferred alkyl groups $R_1$ are $C_1$–$C_3$-alkyl groups, especially $C_1$–$C_2$-alkyl groups.

Alkenyl contains one or more, preferably no more than two, unsaturated carbon-carbon bonds. Examples which may be mentioned are vinyl, allyl, methallyl, prop-1-en-1-yl, 2-methyl-prop-1-en-1-yl and but-2-en-1-yl.

The compounds which are preferred within the scope of the invention are
(1) compounds of formula I, wherein
  $R_1$ and $R_2$ are identical or different and are hydrogen, hydroxyl, amino, halogen, $C_1$–$C_6$-alkyl, halogen-$C_1$–$C_6$-alkyl, $C_1$–$C_6$-alkoxy, nitro, cyano, isothiocyanato, carboxy, $C_1$–$C_6$-alkoxy -carbonyl, $C_1$–$C_6$-alkylcarbamido which is optionally substituted by phenyl or by unsubstituted or halogen-substituted phenoxy; PhNH(CO)NH, $C_1$–$C_6$-alkylsulphonyl, halogen-$C_1$–$C_6$-alkylsulphonyl, benzoyl, phenylthionyl or phenylsulphonyl;
(2) compounds of formula I, wherein
  X is NH O or S;
(3) compounds of formula I, wherein
  Y is $CR_6$ or C=O; and $R_6$ is hydrogen, $C_1$–$C_6$-alkyl, $C_1$–$C_6$-alkylcarbonyl, cyano, 2-di($C_1$–$C_6$-alkyl)aminoethenyl, phenyl, thiazolyl, phenylamino, whereby the phenyl group is unsubstituted or optionally substituted by $C_1$–$C_6$-alkoxy; $C_1$–$C_6$-alkylcarbamido, $C_1$–$C_6$-alkoxycarbamido, guanidiyl, amino, hydroxy-$C_2$–$C_6$-alkylamino or phenylsulphonylamino, whereby the phenyl group is unsubstituted or optionally substituted by $C_1$–$C_6$-alkyl;

(4) compounds of formula I, wherein
Z is N;

(5) compounds of formula I, wherein
$R_1$ and $R_2$ are identical or different and are hydrogen, hydroxyl, amino, halogen, $C_1$–$C_2$-alkyl, halogen-$C_1$–$C_2$-alkyl, $C_1$–$C_2$-alkoxy, nitro, cyano, isothiocyanato, carboxy, ethoxycarbonyl, $C_1$–$C_6$-alkylcarbamido which is optionally substituted by phenyl or by unsubstituted or halogen-substituted phenoxy; PhNH(CO)NH, $C_1$–$C_6$-alkylsulphonyl, halogen-$C_1$–$C_6$-alkylsulphonyl, benzoyl, phenylthionyl or phenylsulphonyl;
$R_3$ and $R_4$ are H or together are a CH=CH—CH=CH— bridge;
X is O or S;
Y is $CR_6$ or C=O;
$R_6$ is hydrogen, $C_1$–$C_6$-alkyl, $C_1$–$C_6$-alkylcarbonyl, cyano, 2-di($C_1$–$C_6$-alkyl)aminoethenyl, phenyl, thiazolyl, phenylamino, whereby the phenyl group is unsubstituted or optionally substituted by $C_1$–$C_6$-alkoxy; $C_1$–$C_6$-alkylcarbamido, $C_1$–$C_6$-alkoxycarbamido, guanidiyl, amino, hydroxy-$C_2$–$C_6$-alkylamino or phenylsulphonylamino, whereby the phenyl group is unsubstituted or optionally substituted by $C_1$–$C_6$-alkyl; and
Z is N;

(6) compounds of formula I, wherein
$R_1$ and $R_2$ are identical or different and are hydrogen, amino, halogen, $C_1$–$C_2$-alkoxy, isothiocyanato, $C_1$–$C_6$-alkylsulphonyl, halogen-$C_1$–$C_6$-alkylsulphonyl or benzoyl;
$R_3$ and $R_4$ are H or together are a CH=CH—CH=CH— bridge;
X is S;
Y is $CR_6$ or C=O;
$R_6$ is $C_1$–$C_6$-alkyl, $C_1$–$C_6$-alkylcarbonyl or 2-di($C_1$–$C_6$-alkyl)aminoethenyl; and
Z is N;

The following compounds of formula I are those which are preferred within the scope of the invention:
X is O or S;
Y is $CR_6$ or C=O;
$R_6$ is hydrogen, $C_1$–$C_6$-alkyl, $C_1$–$C_6$-alkylcarbonyl, cyano, 2-di($C_1$–$C_6$-alkyl)aminoethenyl, phenyl, thiazolyl, phenylamino, whereby the phenyl group is unsubstituted or optionally substituted by $C_1$–$C_6$-alkoxy; $C_1$–$C_6$-alkylcarbamido, $C_1$–$C_6$-alkoxycarbamido, guanidiyl, amino, hydroxy-$C_2$–$C_6$-alkylamino or phenylsulphonylamino, whereby the phenyl group is unsubstituted or optionally substituted by $C_1$–$C_6$-alkyl; and
Z is N;

(6) compounds of formula I, wherein
$R_1$ and $R_2$ are identical or different and are hydrogen, amino, halogen, $C_1$–$C_2$-alkoxy, isothiocyanato, $C_1$–$C_6$-alkylsulphonyl, halogen-$C_1$–$C_6$-alkylsulphonyl or benzoyl;
$R_3$ and $R_4$ are H or together are a CH=CH—CH=CH— bridge;
X is S;
Y is $CR_6$ or C=O;
$R_6$ is $C_1$–$C_6$-alkyl, $C_1$–$C_6$-alkylcarbonyl or 2-di($C_1$–$C_6$-alkyl)aminoethenyl; and
Z is N;

The following compounds of formula I are those which are preferred within the scope of the invention:
2-ethyl-5-methoxy-6-isothiocyanatobenzothiazole,
2-t-butyl-5-methoxy-6-isothiocyanatobenzothiazole,
5-amino-2-methylbenzothiazole,
2-(2-dimethylaminoethenyl)-benzothiazole,
2-propionylbenzothiazole,
4-chloro-2-methylbenzothiazole,
5,6-dimethoxy-2-methylbenzothiazole,
2-methylnaphtho[1,2-d]thiazole,
6-methoxy-2-methylbenzothiazole,
5-trifluoromethylsulphonyl-2-methylbenzothiazole,
6-benzoyl-(2H)-benzoxazolone and
3-acetyl-6-fluoro-(2H)-benzoxazolone;
especially
5-amino-2-methylbenzothiazole and
5,6-dimethoxy-2-methylbenzothiazole.

The invention includes all the compounds of formula I, provided that they are new. General processes for the preparation of compounds of formula I are known. It has been found that benzazole derivatives of formula I are obtained whereby, for example, a) in order to produce compounds of formula I, wherein Y and Z are N, and X, $R_1$, $R_2$, $R_3$ and $R_4$ have the significances given in formula I, a compound of formula

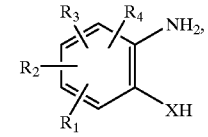

II which is known or may be produced by known processes, and wherein X, Z, $R_1$, $R_2$, $R_3$ and $R_4$ have the significances given in formula I, is reacted with $NaNO_2$ in an aqueous solution containing a mineral acid, or b) in order to produce compounds of formula I, wherein Y is N, Z is $CR_7$, and X, $R_1$, $R_2$, $R_3$ and $R_4$ have the significances given in formula I, a compound of formula

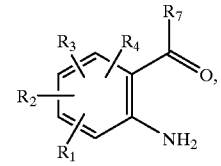

III which is known or may be produced by known processes, and wherein $R_1$, $R_2$, $R_3$, $R_4$ and $R_7$ have the significances given in formula I, is reacted with $NaNO_2$ in an aqueous solution containing a mineral acid, and the resultant intermediate, if necessary after interim isolation, is reduced with a reduction agent such as $SnCl_2$, sodium dithionite or zinc dust in water, or c) in order to produce compounds of formula I, wherein Y is $CR_6$, Z is N, and X, $R_1$, $R_2$, $R_3$ and $R_4$ have the significances given in formula I, a compound of formula II, wherein X, Z, $R_1$, $R_2$, $R_3$ and $R_4$ have the significances given in formula I, is reacted with a compound of formula $QCOR_6$, wherein Q is hydroxyl, $C_1$–$C_2$-alkoxy or halogen, and $R_6$ has the significance given in formula I, or d) in order to produce compounds of formula I, wherein Y is $CR_6$, Z is $CR_7$, and X, $R_1$, $R_2$, $R_3$ and $R_4$ have the significances given in formula I, a compound of formula

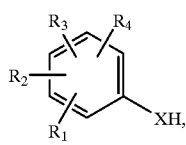

V which is known or may be produced by known processes, and wherein X, $R_1$, $R_2$, $R_3$ and $R_4$ have the significances given in formula I, is reacted with a compound of formula $QC(R_6)C(=O)R_7$, wherein Q is hydroxyl or halogen, and $R_6$ and $R_7$ have the significances given in formula I, or e) in order to produce compounds of formula I, wherein Y is COH, Z is N, and X, $R_1$, $R_2$, $R_3$ and $R_4$ have the significances given in formula I, a compound of formula II is reacted with phosgene or with a carbonic acid dialkylester, or f) in order to produce compounds of formula I, wherein X is O or S, Y is N, Z is $CR_7$ and $R_1$, $R_2$, $R_3$ and $R_4$ have the significances given in formula I, it is reacted with $ClNH_2$, and if desired, a compound of formula I which is obtainable by this process or in another way, or a tautomer thereof, may be converted into another compound of formula I or a tautomer thereof, a mixture of isomers which is obtainable by this process is separated and the desired isomer isolated.

In the process of the present invention, the starting materials and intermediates used are preferably those which lead to the compounds I that were initially portrayed as especially valuable.

Starting materials and intermediates, which are new and are used according to the invention for the preparation of compounds I, as well as their usage and process for the preparation thereof, similarly form an object of the invention.

Although the present benzazole derivatives can of course be mixed with other substances having the same sphere of activity or with parasiticides or with other activity-improving substances to achieve further improved or longer-lasting action, and then applied, in contrast to many compounds of the prior art, this is totally unnecessary, as they already combine all the advantageous properties.

If the parasite is not only to be kept at bay, but also killed, of course this can be achieved by adding appropriate insecticides and/or acaricides. In practice, however, this is unnecessary in most cases.

The present benzazole derivatives are preferably used in diluted form. Normally, they are brought to the final application form by using appropriate formulation excipients, whereby the preparations of the formulations to be applied are produced in known manner by mixing or diluting the active ingredients according to the invention with solvents (e.g. xylene, chlorobenzenes, paraffins, methanol, isopropanol, water), carrier materials (e.g. kaolins, clay, talc, chalk, highly dispersed silicic acid, silicates), emulsifiers (e.g. polyoxyethylene—fatty acid esters, polyoxyethylene fat alcohol ether, alkyl sulphonates, aryl sulphonates) and dispersing agents (e.g. lignin, waste sulphite lye, methyl cellulose).

Since they are in many instances applied to warm-blooded animals and of course come into contact with the skin, suitable formulation excipients are the excipients and administration forms that are known in cosmetics. They may be administered in the form of solutions, emulsions, ointments, creams, pastes, powders, sprays, etc. The preparations generally contain between 0.1 and 95% by weight of active ingredient, preferably between 0.5 and 90%.

For administration to farm animals or pets, the so-called 'pour-on' or 'spot-on' formulations are especially suitable; these liquid or semi-liquid formulations have the advantage that they only have to be applied to a small area of the pelt or plumage, and, thanks to the proportion of spreading oils or other spreading additives, they disperse by themselves over the whole pelt or plumage, without further support, and become active over the whole area.

Of course, inanimate objects, for example human clothing or dog and cat baskets, may be treated with said formulations and thus protected from parasite infestation.

In order to control cockroaches, their locus, usually cracks in the walls, furniture, etc., can be sprayed or powdered.

For the application on humans, a pleasant-smelling essence, e.g. a perfume, can be added to make the application more attractive.

The following examples of preparation and usage of the active ingredients according to the invention serve to illustrate the invention without restricting it.

In particular, preferred formulations are made up as follows:

FORMULATION EXAMPLE 1

A vermin-deterring composition in the form of a lotion for the application to the skin is prepared by mixing 30 parts of one of the active ingredients according to the invention, 1.5 parts of perfume and 68.5 parts of isopropanol, whereby the latter may be replaced by ethanol.

FORMULATION EXAMPLE 2

A vermin-deterring composition in the form of an aerosol for spraying onto the skin is prepared by formulating 50% active ingredient solution, consisting of 30 parts of one of the active ingredients according to the invention, 1.5 parts of perfume and 68.5 parts of isopropanol, with 50% Frigen 11/12 (a halogenated hydrocarbon) as propellant gas in an aerosol can.

FORMULATION EXAMPLE 3

A vermin-deterring composition in the form of an aerosol for spraying onto the skin is prepared by formulating 40% active ingredient solution, consisting of 20 parts of one of the active ingredients according to the invention, 1 part of perfume, 79 parts of isopropanol, with 60% propane/butane (in a ratio of 15:85) as propellant gas in an aerosol can.

Biological Tests

Arena Test Method for Testing Vermin-repellent Substances

This method is carried out in titre plates having 6 wells with a cross-section of 5 cm each, using a computersupported video system. Each well of the titre plate is lined with a circular filter paper or another suitable carrier material. The substance of formula I to be tested is dissolved in methanol, acetonitrile or another suitable solvent, with ultrasound treatment and heating being employed for poorly-soluble substances. In an amount of 1 to 100 mg/cm$^2$, the dissolved test substance is placed in the centre of the filter paper on a quadrant or circular area of ca. 2.4 cm$^2$ radius. 4 of the 6 wells are filled with different test substances or with the same test substance in different dilutions (e.g. 1, 3.2, 5, 10 and 20 mg/cm$^2$). The 5th well is treated with DEET (N,N-diethyl-m-toluamide) as standard substance. The 6th well is filled with the pure solvent and serves as a control. 60 to 100 larvae or 25 to 50 nymphs or 10 to 25 adults of the parasite to be tested, e.g. ticks, are added to each filter paper, and the system is covered with a pane of glass and positioned under a video camera.

At intervals of 5 seconds, the video camera takes individual pictures of all 6 wells. For a qualitative evaluation, these images are observed in a time-lapse as a continuous film, optically following the movements of the parasites on the filter paper and comparing them with the movements in the control well no. 6 or with the standard in the 5th well. A qualitative observation is thus made as to whether the test parasites move evenly over the whole surface of the filter paper and ignore the test substance, or whether and over what period they avoid the treated zone, and what influence the dilution of the test substance has on the behaviour of the test parasites. In this way, neutral and repellent substances are determined. At the same time, the duration of activity of the test substance is determined and compared with that of the standard. By plotting all the images for each individual well over one another, different areas of density are obtained. This represents the frequency at which the parasites visit certain places. This frequency is evaluated statistically and thus quantitatively by the Willcoxon method in a comparison with the control and with the standard.

EXAMPLE A

In vitro Test; Test Animal: *Boophilus microplus* Biarra (Larvae)

The test is carried out as described above, with ca. 60 to 100 larvae being added per well. An evaluation of the video images shows that the compounds according to the invention display marked repellent action. In particular, the compounds 5-amino-2-methylbenzothiazole and 5,6-dimethoxy-2-methylbenzothiazole are notable for an almost complete repellent/deterrent action, which lasts considerably longer than that of DEET.

EXAMPLE B

In vitro Test; Test Animal: *Amblyomma hebraeum* or *variegatum* (Nymphs)

The test is carried out as described above, with ca. 25 nymphs being added per well. An evaluation of the video images shows that the compounds according to the invention display marked repellent action. In particular, the compounds 5-amino-2-methylbenzothiazole and 5,6-dimethoxy-2-methylbenzothiazole are notable for an almost complete repellent/deterrent action, which lasts considerably longer than that of DEET.

EXAMPLE C

In vitro Test; Test Animal: *Rhipicephalus sanguineus* (Nymphs)

The test is carried out analogously to example B, with ca. 40 to 50 nymphs. An evaluation of the video images shows that the compounds according to the invention display marked repellent action. In particular, the compounds 5-amino-2-methylbenzothiazole and 5,6dimethoxy-2-methylbenzothiazole are notable for an almost complete repellent/deterrent action, which lasts considerably longer than that of DEET.

In analogous test set-ups, the same test substances are tested for their attractant activity to various species of fly, such as *Musca domestics*. It is shown that the substances mentioned above display strong repellent action even with these tested models.

What is claimed is:

1. A method for controlling insect, mite or tick infestation on warm-blooded animals, comprising the step of topically applying to said animals a composition comprising a compound selected from the group consisting of 2-ethyl-5-methoxy-6-isothiocyanatobenzothiazole, 2-t-butyl-5-methoxy-6-isothiocyanatobenzothiazole, 5-amino-2-methylbenzothiazole, 2-(2-dimethylaminoethenyl)-benzothiazole, 2-propionylbenzothiazole, 4-chloro-2-methylbenzothiazole, 5,6-dimethoxy-2-methylbenzothiazole, 2-methylnaphtho[1,2-d]thiazole, 6-methoxy-2-methylbenzothiazole, 5-trifluoromethylsulphonyl-2-methylbenzothiazole, 6-benzoyl-(2H)-benzoxazolone and 3-acetyl-6-fluoro-(2H)-benzoxazolone.

2. The method according to claim 1 wherein the compound is selected from the group consisting of 5-amino-2-methylbenzothiazole and 5,6-dimethoxy-2-methylbenzothiazole.

3. A method for repelling insect, mite or tick infestation from warm-blooded animals, comprising the step of topically applying to said animals a repellant composition comprising a compound of formula I

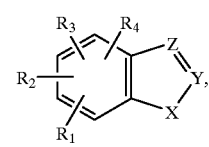

I wherein $R_1$ and $R_2$ are the same or different and signify hydrogen, hydroxyl, amino, halogen, $C_1$–$C_6$-alkyl, halogen-$C_1$–$C_6$-alkyl, $C_2$–$C_6$-alkenyl, halogen-$C_2$–$C_6$-alkenyl, $C_3$–$C_6$-cycloalkyl, halogen-$C_3$–$C_6$-cycloalkyl, $C_1$–$C_6$-alkoxy, halogen-$C_1$–$C_6$-alkoxy, unsubstituted phenyl or phenyl which is optionally substituted by halogen or $C_1$–$C_6$-alkyl; nitro, cyano, isothiocyanato, carboxy, $C_1$–$C_6$-alkoxycarbonyl, halogen-$C_1$–$C_6$-alkoxycarbonyl, $C_1$–$C_6$-alkylcarbamido, which is optionally substituted by phenyl or by unsubstituted or halogen-substituted phenoxy; PhNH(CO)NH, $C_1$–$C_6$-alkylsulphonyl, halogen-$C_1$–$C_6$-alkylsulphonyl, unsubstituted or optionally halogen-substituted benzoyl; unsubstituted or optionally halogen-substituted phenylthionyl or phenylsulphonyl; $R_3$ and $R_4$, independently of one another, are hydrogen, $R_1$, $R_2$ or together are a CH=CH—CH=CH— bridge; X is O or S; Y is N, CR$_6$ or C=O; $R_6$ is hydrogen, hydroxyl, $C_1$–$C_6$-alkyl, $C_1$–$C_6$-alkylcarbonyl, $C_1$–$C_6$-alkoxy, cyano, 2-di($C_1$–$C_6$-alkyl)aminoethenyl, ($C_1$–$C_6$-alkyl)NHC(=S)NHCH$_2$, phenyl, thiazolyl, phenylamino, wherein the phenyl group is unsubstituted or optionally substituted by $C_1$–$C_6$-alkoxy; $C_1$–$C_6$-alkylcarbamido, $C_1$–$C_6$-alkoxycarbamido, guanidyl, amino, hydroxy-$C_2$–$C_6$-alkylamino or phenylsulphonylamino, wherein the phenyl group is unsubstituted or optionally substituted by $C_1$–$C_6$-alkyl; Z is N or CR$_7$; and $R_7$ is hydrogen or $C_1$–$C_6$-alkyl.

4. The method according to claim 3 wherein said compound is selected from the group consisting of 2-ethyl-5-methoxy-6-isothiocyanatobenzothiazole, 2-t-butyl-5-methoxy-6-isothiocyanatobenzothiazole, 5-amino-2-methylbenzothiazole, 2-(2-dimethylaminoethenyl)-benzothiazole, 2-propionylbenzothiazole, 4-chloro-2-methylbenzothiazole, 5,6-dimethoxy-2-methylbenzothiazole, 2-methylnaphtho[1,2-d]thiazole, 6-methoxy-2-methylbenzothiazole, 5-trifluoromethylsulphonyl-2-methylbenzothiazole, 6-benzoyl-(2H)-benzoxazolone and 3-acetyl-6-fluoro-(2H)-benzoxazolone.

5. The method according to claim 3 wherein said compound is selected from the group consisting of 5-amino-2-methylbenzothiazole and 5,6-dimethoxy-2-methylbenzothiazole.

* * * * *

UNITED STATES PATENT AND TRADEMARK OFFICE
CERTIFICATE OF CORRECTION

PATENT NO. : 6,410,578 B1
DATED : June 25, 2002
INVENTOR(S) : Bouvier et al.

It is certified that error appears in the above-identified patent and that said Letters Patent is hereby corrected as shown below:

<u>Title page</u>
Item [63], Related U.S. Application Data, should read:
-- This case is a continuation of prior application no. PCT/EP99/04173, filed June 16, 1999 --.

Signed and Sealed this

Thirty-first Day of January, 2006

JON W. DUDAS
*Director of the United States Patent and Trademark Office*